US008765369B2

(12) United States Patent
Dubus et al.

(10) Patent No.: US 8,765,369 B2
(45) Date of Patent: Jul. 1, 2014

(54) ULTRASENSITIVE DETECTION OF TARGET USING TARGET-READY PARTICLES

(75) Inventors: Sebastien Dubus, Québec (CA); Hoang-Anh Ho, Laval (CA); Mario Leclerc, Québec (CA); Denis Boudreau, Sainte-Foy (CA)

(73) Assignee: National Research Council of Canada, Ottawa (CA)

( * ) Notice: Subject to any disclaimer, the term of this patent is extended or adjusted under 35 U.S.C. 154(b) by 751 days.

(21) Appl. No.: 12/668,388

(22) PCT Filed: Jul. 11, 2008

(86) PCT No.: PCT/CA2008/001299
§ 371 (c)(1),
(2), (4) Date: Nov. 23, 2010

(87) PCT Pub. No.: WO2009/009889
PCT Pub. Date: Jan. 22, 2009

(65) Prior Publication Data
US 2011/0091874 A1    Apr. 21, 2011

Related U.S. Application Data

(60) Provisional application No. 60/929,825, filed on Jul. 13, 2007.

(51) Int. Cl.
C12Q 1/68    (2006.01)
C07H 21/00   (2006.01)
C07H 21/02   (2006.01)
C07H 21/04   (2006.01)

(52) U.S. Cl.
USPC ......... 435/6.1; 536/23.1; 536/24.3; 536/25.3; 536/26.6

(58) Field of Classification Search
USPC ............... 435/6.1; 536/23.1, 24.3, 25.3, 26.6
See application file for complete search history.

(56) References Cited

U.S. PATENT DOCUMENTS

| | | | |
|---|---|---|---|
| 5,821,066 A | 10/1998 | Pyle et al. | 435/7.2 |
| 6,544,746 B2 | 4/2003 | Heyduk | 435/6.16 |
| 7,083,928 B2 * | 8/2006 | Leclerc et al. | 435/6.11 |
| 7,214,489 B2 | 5/2007 | Bazan et al. | 435/6.11 |
| 7,270,956 B2 | 9/2007 | Bazan et al. | 435/6.19 |
| 2004/0029143 A1 | 2/2004 | Van Ness et al. | 435/6.19 |
| 2004/0265823 A1 | 12/2004 | Maruyama | 435/6.14 |
| 2005/0003386 A1 | 1/2005 | Bazan et al. | 435/6.11 |

(Continued)

FOREIGN PATENT DOCUMENTS

| | | |
|---|---|---|
| EP | 1586904 | 10/2005 |
| WO | WO 2006/092063 | 9/2006 |
| WO | WO 2007/131354 | 11/2007 |

OTHER PUBLICATIONS

Dubus et al. Anal. Chem. 2006, 78, 4457-4464.*

(Continued)

Primary Examiner — Jezia Riley
(74) Attorney, Agent, or Firm — Fulbright & Jaworski LLP

(57) ABSTRACT

The invention relates to methods and reagents for detecting minute amounts of targets having affinity for nucleic acid. The present invention more particularly relates to target detection using aggregates of cationic polymer chains and nucleic acid capture probes linked to particles, such as controllable mobility particles.

55 Claims, 6 Drawing Sheets

(56) References Cited

U.S. PATENT DOCUMENTS

| | | | |
|---|---|---|---|
| 2006/0160124 A1 | 7/2006 | Leclerc et al. | 435/6.11 |
| 2006/0183140 A1 | 8/2006 | Bazan et al. | 435/6.11 |
| 2006/0216734 A1 | 9/2006 | Bazan et al. | 435/6.11 |
| 2007/0178470 A1 | 8/2007 | Bissonnette et al. | 435/6.11 |
| 2007/0196825 A1 | 8/2007 | Leclerc et al. | 435/6.11 |
| 2008/0064042 A1 | 3/2008 | Bazan et al. | 435/6.11 |

OTHER PUBLICATIONS

Najari et al. Analytical Chemistry, vol. 78, No. 22, pp. 7896-7899.*

Aberem et al. Advanced Materials 2006, vol. 18, No. 20, pp. 2703-2707.*

Dalgleish et al., "A possible structure of the casein micelle based on high resolution field-emission scanning electro microscopy," *Int. Dariy J.*, 14: 1025-1031, 2004.

Doré et al., "Characterization of superlightning polymer—DNA aggregates: a fluorescence and light scattering study," *Langmuir*, 23 (1): 258-264, 2007.

Doré et al., "Fluorescent polymeric transducer for the rapid, simple, and specific detection of nucleic acids at the zeptomole level," *J. Am. Chem. Soc.*, 126 (13): 4242-4244, 2004.

Doré et al., "Investigation of a fluorescence signal amplification mechanism used for the direct molecular detection of nucleic acids," *J. Fluoresc.*, 16 (2): 259-265, 2006.

Ho et al., "Colorimetric and Fluorometric Detectrion of Nucleic Acids Using Cationic Polythiophene Derivatives", *Communications: Angew. Chem. Int. Ed.*, 41(9):1548-1551, 2002.

Ho et al., "Direct molecular detection of nucleic acids by fluorescence signal amplification," *J. Am. Chem. Soc.*, 127 (36): 12673-12676, 2005.

Ho et al., "Optical detection of DNA and proteins with cationic polythiophenes," *Accounts of Chemical Research*, 41 (2): 168-173, 176, 2008.

Ibrahim et al., "Flow Cytometry and Cell Sorting", *Adv. Biochem. Engin. Biotechnol.*, 106:19-39, 2007.

International Preliminary Report on Patentability, in Int. App. No. PCT/CA2008/001299, mailed Nov. 4, 2009.

International Search Report and Written Opinion, in Int. App. No. PCT/CA2008/001299, mailed Oct. 2, 2008.

Peytavi et al., Correlation between microarray DNA hybridization efficiency and the position of short capture probe on the target nucleic acid, *Biotechniques*, 39 (1): 89-96, 2005.

\* cited by examiner

ULTRASENSITIVE DETECTION OF TARGET USING TARGET-READY PARTICLES

CROSS-REFERENCE TO RELATED APPLICATIONS

The present application is a national phase application under 35 U.S.C. §371 of International Patent Application PCT Application No. PCT/CA2008/001299, filed 11 Jul. 2008, which claims the benefit of U.S. Provisional Application No. 60/929,825, filed 13 Jul. 2007. The entire contents of these applications are incorporated by reference.

FIELD OF THE INVENTION

The present invention relates to methods and reagents for detecting minute amounts of targets having an affinity for nucleic acids. The present invention more particularly relates to target detection using aggregates of cationic polymer chains and nucleic acid capture probes linked to particles, such as controllable mobility particles.

BACKGROUND OF THE INVENTION

The development of fast and reliable DNA biosensors is of critical importance for the diagnostics/detection of infectious agents, for the identification of genetic mutations, for forensic investigations or food quality control, and will very likely continue to grow in the foreseeable future. Several sensitive approaches based on optical, electrochemical or magnetoresistive detection were reported over the years. Relatively few of these methods, however, offer the simultaneous advantages of simplicity, specificity, sensitivity and rapidity of detection without the use of chemical tagging of the DNA target or polymerase chain reaction (PCR) amplification.

A cationic polymeric transducer was previously reported to adopt distinct conformation when electrostatically bound to either ssDNA (single-stranded DNA) or dsDNA (double-stranded DNA) (U.S. Pat. No. 7,083,928). This technology allows optical detection of DNA material by fluorescence measurement in homogeneous medium, but is not as sensitive as desired (JACS 2004, 126, 4242-4244).

Further developments led to a combination of the cationic polythiophene with fluorophore-tagged ss-DNA probes to form a micellar system in which a Resonant Energy Transfer (RET) process leads to an amplification of the fluorescence signal emitted in the presence of target DNA material. This detection scheme, called "Fluorescence Chain Reaction" or FCR, allowed the optical detection by fluorescence of as few as 5 molecules of purified DNA from homogenous aqueous solution in only five minutes, and led to the first-ever demonstration of the direct detection of single nucleotide polymorphisms (SNPs) from clinical samples in such a short time, without the need for any nucleic acid amplification such as PCR (WO 2006/092063 A1, Leclerc et al.; JACS, 2005, 127, 12673-12676). However, the formation and evolution/conservation of micelles being dynamic phenomena, FCR relies on a particular arrangement of the fluorescent species within the self-assembled micelle-like aggregates which was shown to be strongly dependent on conditions of concentration, temperature and ionic strength in aqueous media (Langmuir, 2007, 23, 258-264). Therefore, improvements in the method to provide stabilization of the aggregates towards chemical and physical changes in their local environment and hence greater robustness are needed to ensure more reproducible analytical results.

It was recently shown that aggregates similar to those reported previously could be immobilized on a 2D solid support for DNA detection (international application NO.: PCT/CA2007/000857 published on Nov. 22, 2007 under No. WO2007/131354, Anal. Chem., 2006, 78, 7896-7899). The aggregates were covalently linked to the surface of a glass slide. Thus prepared, the slide displayed RET signal amplification (showing that the FCR behaviour of the aggregates was retained after the grafting process) and could be stored for extended periods in the dark and a dry atmosphere. After hybridizing with target DNA for 60 minutes, washing with a surfactant solution and water and finally drying the slides, the fluorescence signal was collected by a conventional microarray reader. However, whereas a molecular detection limit of 300 20-mer DNA target molecules was reported for 0.4-µL sample droplets, the volumetric detection limit reported for glass slide based FCR is significantly poorer than that reported for FCR detection in homogenous media ($5 \times 10^{-16}$ vs. $3 \times 10^{-21}$ mole/L, respectively). Given that the majority of infectious diseases need to be diagnosed promptly in order to be curable and only a few pathogens are usually present in the blood or sputum (with sample volumes ranging from a few tens of µL to a few mL) at the onset of an infection, the volumetric detection sensitivity provided by glass slide based FCR is insufficient for PCR-free detection of such low levels of DNA material. Furthermore, detection of genomic DNA material (i.e. longer DNA chains typical of those found in clinical or biological samples), which is usually more difficult due to steric hindrance and rehybridization of the free overhanging tail of the capture DNA strand with its complementary strand (Peytavi et al, Biotechniques 2005), was not demonstrated with glass slide based FCR.

The poorer volumetric detection limit and longer hybridization time of glass slide FCR vs. homogenous FCR betray an inherent limitation of the 2D microarray-based format, i.e. the finite speed of diffusion of target molecules towards the immobile glass slide surface and the grafted aggregates is the key limiting factor when attempting to transfer FCR detection from homogeneous media to a static solid support while still retaining the former's detection speed and sensitivity. Because of this finite speed of diffusion, extending the application of this detection scheme to larger sample volumes would only result in poorer molecular detection limits. In other words, the procedure used to expose the sample to the grafted aggregates (deposition of individual microdroplets of sample over each grafted spot) cannot be extended to larger sample volumes without incurring signal losses due to incomplete analyte extraction from the sample.

Furthermore, the procedure used to graft the micelle-like aggregates onto the slides requires numerous chemical steps in different aqueous media as well as exposure of the grafted aggregates to the atmosphere and drying. Examples abound in the literature that underline the paramount importance of the experimental protocol used to deposit micelles of various types on slides for their microscopic examination, and in particular in the care needed when going from an aqueous to an organic and finally to a dry environment, in order to preserve their structural integrity and activity (Int. Dairy J. 2004, 14, 1025-1031). Since FCR signal amplification is known to hinge on a particular arrangement of fluorophores within the aggregates, which brings the fluorophore acceptors in close proximity to each other (Langmuir 2007, 23, 258-264; J. Fluoresc. 2006, 16, 259-265), it is thus desirable to transfer the aggregates in the native form obtained in solution onto a solid support in such a way that their photonics properties will not be altered. Therefore, the poorer detection sensitivity of slide based FCR vs. homogenous FCR could also be attributable in part to a modification in the conformation of the aggregates (form, size, density) caused by the drastic changes in the environment of the aggregates during their transfer from the homogenous solution to the slide surface.

Micrometer- or nanometer-sized particles or beads are commonly used for the detection of biomolecules. Most applications involve ss-DNA probes (labeled or unlabeled) that are covalently grafted on the beads (U.S. Pat. No. 6,544, 746B2) These beads may then be manipulated or concentrated, usually by means such as magnetic fields or filtration. Capture of the targets by these probes is typically followed by the transduction of the "probe-target" recognition event (for example, using a minor groove intercalator for the double DNA helix, or a sandwich assay approach) (U.S. Pat. No. 5,821,066). However, since bead-based detection does not in itself procure an amplification of the optical signal, detection of ultralow levels of DNA material still requires prior amplification of the target sought to be detected It was recently shown by Dubus et al. that DNA detection using the polythiophene transducer described previously was achievable directly on particles either using highly diluted suspension, i.e. homogeneous dispersion of the particles in solution or by confining particles in a small detection volume (Anal. Chem. 2006, 78:4457-4464). This approach, though sensitive and specific, does not meet the level of sensitivity reported for the technique known as FCR.

There thus remain a need to improve tools and methods for detection of nucleic acid and protein targets.

The present invention seeks to meet these needs and other needs.

SUMMARY OF THE INVENTION

Detection of targets using new tools and methods is described herein.

The present invention relates in one aspect thereof to a particle which may comprise aggregates formed by a nucleic acid probe and a cationic polymer.

In accordance with the present invention, the cationic polymer may comprise formula A

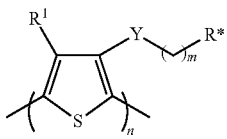

(formula A)

wherein m may be an integer ranging for 2 to 3;

n may be an integer ranging from 3 to 100;

R* may be a quaternary ammonium;

Y may be an oxygen atom or a methylene; and $R^1$ may be a methyl group or a hydrogen atom.

Particular embodiments of polymers which may be used to carry the present invention are those, for example, where m is 3, R* is $^+NEt_3$; Y is an oxygen atom; and $R^1$ is a methyl group.

Other particular embodiments of polymers which may be used to carry the present invention are those, for example, where m is 2, Y is an oxygen atom, $R^1$ is a methyl group and R* is

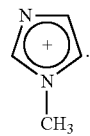

Yet other particular embodiments of polymers which may be used to carry the present invention are those where m is 2, Y is an oxygen atom, $R^1$ is a methyl group and R* is

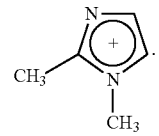

Further particular embodiments of polymers which may be used to carry the present invention are those, for example, where m is 2, Y is a methylene group, $R^1$ is a hydrogen atom, and R* is

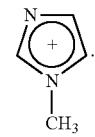

In accordance with the present invention, the polymer of formula A may be particularly selected from the group consisting of:

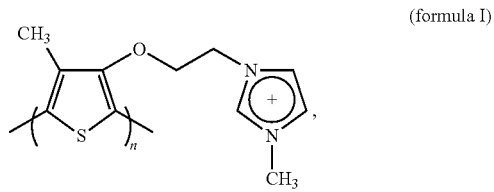

(formula I)

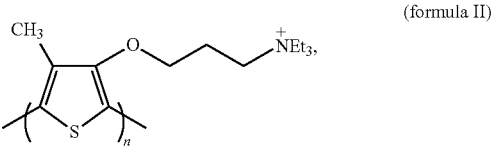

(formula II)

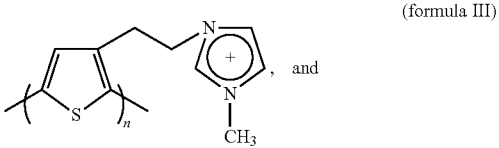

(formula III)

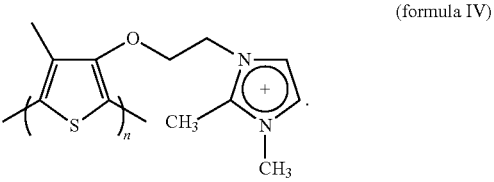

(formula IV)

The present invention more specifically relates in an aspect thereof to a particle which may comprise aggregates formed by a nucleic acid probe and a polymer of formula Ia

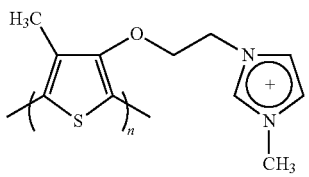

Ia wherein n is an integer ranging from 6 to 100 (or any sub-ranges, e.g., 6 to 75, 6 to 50, 10 to 55, 35 to 45, for example, n may be 20, 30, 40, 41, 42, 45 etc.). The particles may be coated with the aggregates.

In an embodiment of the invention, the nucleic acid probe may preferably be single-stranded but may also be double-stranded. The aggregates may be in association with the particle's surface. In an exemplary embodiment, the aggregates may be attached to the particles via the nucleic acid probe, whereas the cationic polymer may simply be in electrostatic interaction with the nucleic acid probe. In an alternative embodiment, the aggregates may be attached to the particles via the polymer, whereas the nucleic acid probe would be in electrostatic interaction with the cationic polymer. The photonic and sensing properties of the aggregates would be retained in this alternate configuration. In an embodiment of the invention the nucleic acid probe may comprise a label.

The complex formed by the nucleic acid probe and the polymer may be stoichiometric or not.

Particles carrying the aggregates are identified herein as "target-ready particles".

The particles (target-ready particles) may possess properties allowing for its isolation from a suspension. The particle's mobility may be controllable by means known in the art. For example, the particle may be magnetic (paramagnetic) and its mobility may thus be controlled by a magnet (in a magnetic field). As another example, the size or inertia of a non magnetic particle might be used to steer it by means of hydrodynamic or microfluidic flow control. In all cases, concentration of the particles in a smaller detection volume or area would allow to maximize the ratio of fluorescence signal emitted by the particles to the background signal generated by the solvent (Raman or Rayleigh scattering) or neighboring solid surfaces (scatter or autofluorescence).

The controllable mobility combined with the FCR properties of the aggregates linked to particles allows for ultrasensitive target detection compatible with microfluidic systems and devices.

The particle (e.g., particle core) used to carry and stabilize the FCR aggregates can be tagged (i.e, may comprise a tag) or coded, using various signaling entities such as fluorophores, to code the particular DNA probe sequence composing the aggregates. FCR beads targeting different DNA sequences (e.g. targeting distinct mutations in a human genomic DNA sample) could thus be released together in a sample and, after a time adequate for target capture has elapsed, separated by flow cytometry techniques in a microfluidic apparatus (PCT/FR2007/051461 published on Dec. 27, 2007 under No. WO 2007/148013 A1; S. F. Ibrahim and G. van den Engh, "Flow cytometry and cell sorting", Adv. Biochem. Engin. Biotechnol. (2007), 106, 19-39) and finally detected by FCR. The combination of the multicomponent analysis capacity provided by such coded particle cores with the high detection sensitivity of FCR and the capacity of particle-grafted FCR aggregates to efficiently capture target molecules from large sample volumes, could ultimately lead to PCR-free, multi-target DNA analysis of as little as a few target DNA molecules from extended sample volumes.

Further scope and applicability will become apparent from the detailed description given hereinafter. It should be understood, however, that this detailed description, while providing exemplary embodiments of the invention, is given by way of example only, since various changes and modifications will become apparent to those skilled in the art.

DETAILED DESCRIPTION

Figure 1:
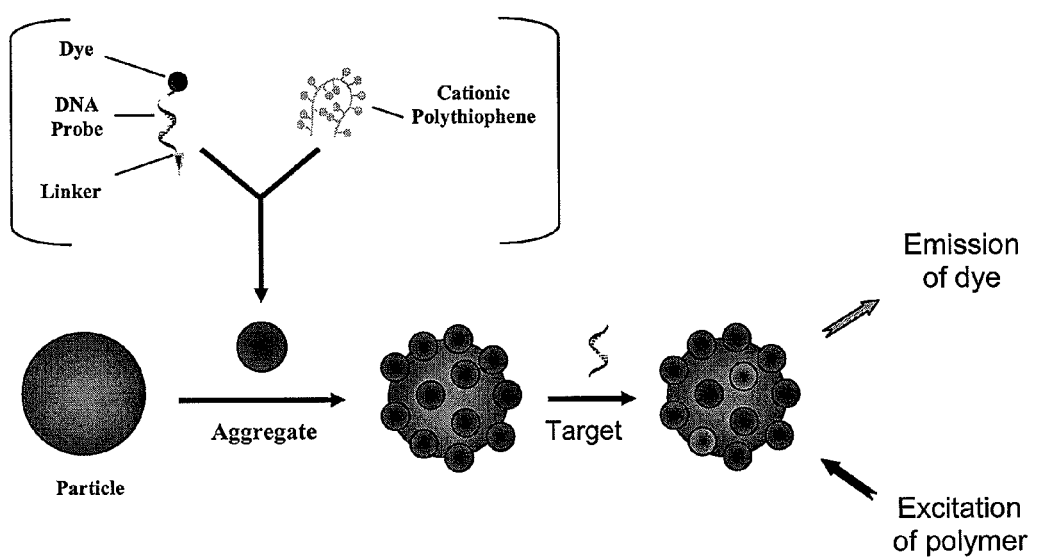
FIG. 1 is a schematic description of the invention. In a first step, dye-labeled and linker-functionalized probe is associated with polythiophene to form duplex aggregates which are then linked to mobile particles. Recognition of target ss-DNA by duplex aggregates occurs onto the target-ready particles. Visualization of signal amplification detection mechanism is based on the conformation change of cationic polythiophene and subsequent energy transfer.

The present invention more specifically relates to particles (microsphere, beads, nanosphere, nanotubes, nanorods, etc.) which may comprise an aggregate formed by a nucleic acid capture probe and a cationic polymer of any of formula A, I, Ia, II, III and/or IV. The present invention more specifically relates to particles which may comprises a polymer of formula Ia as indicated herein.

It has been shown herein that the particle of the present invention may advantageously detect a target at a concentration as low as $10^{-16}$ mole/L, $10^{-17}$ mole/L, $10^{-18}$ mole/L and even $10^{-19}$ mole/L.

It has been found that the detection may be carried out without prior amplification of the target, i.e., using unamplified target and without prior labelling of the target, i.e., using unlabelled target.

The capture probe may be selected, for example, from the group consisting of DNA, RNA and may comprise a portion or section of nucleic acid sequence for specific recognition to the desired target while avoiding interaction with unspecific molecules. It is to be understood herein that the section of interaction between probe and target can either cover the entire length of the probe and/or target, or be shorter or longer than said probe and/or target.

In the case of detection of nucleic acid-based target, the section of interaction between the probe and target may comprise a nucleotide/nucleoside sequence which is complementary or substantially complementary to one another. In one particular embodiment the section of interaction between the probe and the nucleic acid-based target comprises a nucleotide/nucleoside sequence which is complementary to one another. The probe may also be designed to comprise an aptameric portion able to bind a protein or a small molecule of interest. The length and nature of this aptameric portion may vary according to the type of molecule targeted. The section of interaction may comprise at least 8 consecutive bases (nucleotides/nucleosides or analogues). The section of interaction may vary from about 8 to about 50 bases (or any sub-range, e.g., 15 to 50, 20 to 45, etc.), although other lengths may suitably be used without departing from the scope of the invention. The section of interaction may cover the total length of the probe and/or target. In an embodiment of the invention, the probe may comprise at least 8 consecutive bases which are perfectly complementary to 8 bases of the target.

The total length of the nucleic acid capture probe may vary from about 8 to about 50 bases, although other lengths may suitably be used without departing from the scope of the invention.

Although for purpose of concision, the complete list of combination of length between 8 to 50 nucleotides long is not provided herein it is intended that each and every possible combinations that may be found between 8 to 50 nucleotides (inclusively) be covered, including for example, 15 to 50, 20 to 45, etc.

In another embodiment of the invention, the probe and/or the section of target-probe interaction may be at least 8 bases long, at least 9 bases long, at least 10 bases long, at least 11 bases long, at least 12 bases long, at least 13 bases long, at least 14 bases long, at least 15 bases long, at least 16 bases long, at least 17 bases long, at least 18 bases long, at least 19 bases long, at least 20 bases long, at least 21 bases long, at least 22 bases long, at least 23 bases long, at least 24 bases long, at least 25 bases long, at least 26 bases long, at least 27 bases long, at least 28 bases long, at least 29 bases long, at least 30 bases long, at least 31 bases long etc.

In order to maximize the analytical signal, the nucleic acid capture probes may be labelled. Detectable labels suitable for use in the present invention include molecules detectable by spectroscopic, photochemical, biochemical, immunochemical, electrical, optical or chemical means. Useful labels in the present invention include chromophores, fluorophores, biotin for staining with labeled streptavidin conjugate, fluorescent dyes (e.g., fluorescein, Texas Red, rhodamine, green fluorescent protein, and the like), radiolabels (e.g., $^3$H, $^{125}$I, $^{35}$S, $^{14}$C, or $^{32}$P), phosphorescent labels, enzymes (e.g., horse radish peroxidase, alkaline phosphatase and others commonly used in an ELISA). Fluorescent labels may easily be added during synthesis of the probe and thus represent an interesting avenue.

An acceptor molecule having both a high fluorescence quantum yield and a good spectral overlap between its absorption spectra and the emission spectra of the cationic polymer described herein may be more particularly selected. An exemplary embodiment of such a fluorescent acceptor which is encompassed by the present invention is, without limitation: AlexaFluor546, Cy3, quantum dot, etc.

The nucleic acid capture probe may be in association to the mobility controllable particle by means which are known in the art and which are not intended to be limitative. In an exemplary embodiment the probe may be attached through a linker moiety, either by its 3'-end or by its 5'-end. It is to be understood herein that the linker moiety may allow for the permanent attachment or for the temporary attachment of the nucleic acid capture probe to the surface of the mobility controllable particle. It is also to be understood herein that the linker moiety may allow for the reversible attachment or for the irreversible attachment of the nucleic acid capture probe to the surface of the mobility controllable particle. As such, the linker moiety between the aggregate and the particle may be of covalent type, key-lock type (affinity interaction), or any other type of bond which ensures a stable (in the time scale of detection) anchoring of the aggregates to the surface of the particle without departing from the scope of the invention.

In an exemplary embodiment of the invention, different nucleic acid capture probes may be attached to distinct particles allowing several target species to be detected at the same time in a mixture. Particle distinction and target identification and/or isolation in a mixture may be achieved for example, by the use of a different label for each capture probe species (differing either in its spectral signature or in its luminescence lifetime decay), by the use of different size of particles for each capture probe species, by tagging the particle, etc. Specific particles are preferably associated with specific (i.e., identical) and predetermined probes allowing later identification of the target that is being captured.

Attaching different probes to the same particle may also be found useful. For example, the particles may be used for removing undesired component from a sample, such as in the case of blood purification during dialysis or for isolating desired components from a mixture. A particle carrying different aggregates may thus be used to remove or isolate several targets at the same time.

The particles of the present invention may also be found useful for affinity chromatography.

Another significant advantage of the present invention is that particles may be sorted (e.g. by using magnetic particles and magnets) prior to or after detection of the target thus allowing isolation of the targets and if so desired, their purification by discarding non specific target material or other contaminants. Sorting may be also performed based on the signal emitted once the target is bound to the aggregates. Each particle may thus be detected individually (flow cytometry or single molecule detection conditions, for example) on the basis of its optical properties (diffusion, absorption, fluorescence intensity or lifetime, scattering) and on the basis of aggregates spectral properties. This approach allows a high degree of multiplexing in the analysis of multiple targets.

The present invention also relates to a composition comprising the particle described herein and an aqueous solution.

More particularly, in an aspect the invention provides a composition which may comprise multiple particle species in solution. Each particle species may comprise aggregates formed by the association of a distinct nucleic acid probe species and a polymer of formula A, formula I, formula II, formula III and/or formula IV and wherein the aggregates are in association with a surface of the particle.

A particular embodiment of the invention relates to a composition which may comprise multiple particle species, where each particle species comprises aggregates formed by the association of a distinct nucleic acid probe species and a polymer of formula Ia

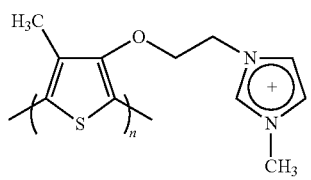

wherein n is an integer ranging from 6 to 100 and wherein the aggregates are in association with a surface of the particle.

In accordance with the present invention, each nucleic acid probe species may comprise a distinct nucleotide/nucleoside sequence.

Also in accordance with the present invention, each nucleic acid probe species may independently be single-stranded or double stranded.

Further in accordance with the present invention, each probe species may independently comprise RNA or DNA.

Also in accordance with the present invention, each probe species may independently comprise from 8 to 50 bases.

In accordance with the present invention each particle species may comprise a distinct tag allowing identification of the nucleic acid probe species associated with the particle species.

The present invention also provides in a further aspect thereof, to kits for the detection, isolation or identification of a target or multiple target species. The kit may comprise several particle species where each particle species may be provided separately or may be provided as a mixture. The particles may be provided in solution (e.g., an aqueous solution).

A "probes species" relates to a probe which is distinct from another probe in the area of interaction with its target. By "structurally distinct" it is meant, in the case of probes, that the nucleotide/nucleoside sequence of one species is different from the nucleotide/nucleoside sequence of the other species in at least one nucleotide in the area of interaction with the target.

A "target species" relates to a target which is structurally distinct from another by at least one element (e.g., a nucleotide, an amino acid, a substituent, etc.).

By "structurally distinct" it is meant, in the case of nucleic acid-based target, that the nucleotide/nucleoside sequence of one species is different from the nucleotide/nucleoside sequence of the other species in at least one nucleotide in the area of interaction with the probe. In the case of protein-based target, "structurally distinct" means that the amino acid sequence of one species is different from the amino acid sequence of the other species in at least one amino acid in the area of interaction with the probe.

A "particle species" relates to a particle carrying a specific probe species.

It is to be understood herein that each and every characteristics provided for targets, probes, particles, aggregates, also apply to target species, probe species, particles species or aggregates species. When the invention relates to methods and reagents comprising multiple species, the characteristics of the target species may be different (independent) or the same as the characteristics of the other target species. The same is true for probe species, particles species and aggregates species, wherein the characteristics of the probe species, particles species and aggregates species may be different (independent) or the same as the characteristics of the other probe species, particles species or aggregates species.

As used herein the term "at least 8" encompasses, "at least 8", "at least 9", "at least 10", "at least 11", "at least 12", "at least 13", "at least 14", "at least 15", "at least 16", "at least 17", "at least 18", "at least 19", "at least 20", "at least 21", "at least 22", "at least 23", "at least 24", "at least 25", "at least 26", "at least 27", "at least 28", "at least 29", "at least 30", "at least 31", "at least 32", etc.

Any molecule having a specific affinity (and/or specificity) for a given sequence of nucleic acids may be considered a target and may advantageously be detected using the invention provided herein. Targets which may advantageously be detected are those having affinity for nucleic acids and include, without limitation, nucleic acids, proteins, protein complexes, peptides, small molecules, ions, vitamins, chromophores, coenzymes, amino acids and derivative, antibiotics, synthetic drugs, etc.

Targets may thus comprise, for example, biopolymers such as DNA, RNA or DNA/RNA chimeras (e.g., nucleic acids). The target may be a single-stranded polynucleotide, a double-stranded polynucleotide, or higher order (e.g., triplex), and can be linear or circular. Exemplary single-stranded target polynucleotides include mRNA, rRNA, tRNA, hnRNA, ssRNA or ssDNA viral genomes, although these polynucleotides may contain internally complementary sequences and significant secondary structure. Exemplary double-stranded target polynucleotides include genomic DNA, mitochondrial DNA, chloroplast DNA, dsRNA or dsDNA viral genomes, plasmids, phage, viroids and fragments thereof. The target (e.g., polynucleotide, polypeptide, etc.) can be prepared synthetically (e.g., PCR amplicon) or purified from a biological source (e.g., restriction fragment). When the target is, for example, double-stranded, it may be rendered single-stranded (e.g., by denaturation, enzymatic degradation or else) prior to being contacted with the target ready particles. The target (e.g., polynucleotide, polypeptide, etc.) may also be purified to remove or diminish one or more undesired components of the sample or to concentrate the target (e.g., polynucleotide, polypeptide, etc.).

The target may also comprise a protein or any other molecule which is capable of specific binding to a nucleic acid sequence (e.g., aptamer, transcription sites, etc.). Exemplary embodiments of target protein includes for example and without limitation, transcription factors, RNA or DNA Polymerases, ligases, integrases, recombinases etc. Alternatively, nucleic acid libraries may be screened using a desired protein or molecule of interest to select a specific sequence which in turn may be used for generating detection tools for identifying, quantifying, isolating the desired protein or molecule from a sample using the present invention.

The sample comprising or suspected of comprising the target may be of any source of material, originating or isolated for example, from plants, mammals, insects, amphibians, fish, crustaceans, reptiles, birds, bacteria, viruses, archaeans, food, etc. or from an inorganic sample onto which a target has been deposited or extracted (forensic, objects, rocks, etc.). Biological material may be obtained from an organism directly or indirectly, including cells, tissue or fluid, and the deposits left by that organism, including viruses, mycoplasma, and fossils. The sample may comprise a target prepared through synthetic means, in whole or in part. Non-limiting examples of the sample may include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, tumors, organs, samples of in vitro cell culture constituents (including but not limited to conditioned medium resulting from the growth of cells in cell culture medium, putatively virally infected cells, recombinant cells, and cell components), and a recombinant library comprising polynucleotide sequences.

The sample may be diluted, dissolved, suspended, extracted or otherwise treated to solubilize and/or purify any putative target present or to render it accessible to reagents which are used in an amplification scheme or to detection reagents. Where the sample contains cells, the cells may be lysed or permeabilized to release the target from within the cells. The sample may preferably be in a liquid state. Detection may be advantageously performed in highly diluted suspensions, i.e. homogeneous dispersions of the particles in solution (see results FIG. 2).

The particle's mobility may be controllable or not depending on the needs of the user. The particle may be of various composition: polymer, silica, metallic (quantum dots for example), inorganic (silicon, diamond), composite etc., of various architectures: solid, hollow (including micellar, colloidal or liposome structure), core-shell, multi-layer, multi-core, comporting magnetic core, dye (simple or multiple) containing core/shell etc., of various shapes (spheres, cubes, triangles, etc.) and of various sizes from nano- to micrometric scale without departing the scope of the invention. As used herein the term "particle" therefore encompasses, beads, microspheres, nanospheres, nanotubes, etc.

Other aspects of the invention relates to methods for detecting, quantifying, isolating or purifying a target using the target-ready particle of the present invention.

The detection method of the present invention may comprise for example, contacting a sample comprising the target or susceptible of comprising the target with the target-ready particle of the present invention and measuring a signal emitted upon (a conformational change associated with a) specific binding between the nucleic acid probe and the target. More particularly, the particles may be suspended in a liquid media comprising the sample and interaction between the target and the aggregate is allowed to proceed.

Moreover, other aspects of the present invention relates to methods of detecting the presence or absence of a target, of isolating the target from the sample, of identifying the target or else.

The present invention thus provides a method for detecting the presence or absence of a target in a sample comprising or suspected of comprising the target, the method may comprise:
contacting the sample with a particle comprising an aggregate (the aggregate being associated with the particle) formed by the association of a nucleic acid probe and a polymer of formula A, formula I, Ia, II, III and/or IV allowing sufficient period of time for the target to bind the nucleic acid probe and;
measuring or identifying a signal emitted upon binding of the target and the nucleic acid probe (i.e., upon binding of the target to the aggregate).

The present invention more particularly relates to a method for detecting the presence or absence of a target in a sample comprising or suspected of comprising the target by:
contacting the sample with a particle which comprises an aggregate formed by the association of a nucleic acid probe and a polymer of formula Ia;
allowing sufficient period of time for the target to bind the nucleic acid probe and;
measuring or identifying a signal emitted upon binding of the target and the nucleic acid probe (i.e., upon binding of the target to the aggregate).

Methods of the present invention also encompass the simultaneous detection of multiple target species from a sample, the method may comprise:
contacting the sample with a composition comprising multiple particle species, where each particle species comprises aggregates (in association with the particles) formed by the association of a distinct nucleic acid probe species and a polymer of formula A, formula I, formula Ia, formula II, formula III and/or formula IV:
allowing sufficient period of time for the target species to bind the nucleic acid probe species and;
measuring or identifying a signal emitted upon binding of the target species and the nucleic acid probe species.

In accordance with the present invention, each particle species may further comprise a distinct and selectable tag allowing its distinction among the multiple particle species.

In a more particular embodiment, the present invention provides a method for the simultaneous detection of multiple target species from a sample, the method may comprise:
contacting the sample with a composition comprising multiple particle species, where each particle species comprises aggregates (in association with the particles) formed by the association of a distinct nucleic acid probe species and a polymer of formula Ia,
allowing sufficient period of time for the target species to bind the nucleic acid probe species and; measuring or identifying a signal emitted upon binding of the target species and the nucleic acid probe species,
wherein each particle species may further comprise a distinct and selectable tag allowing its distinction among the multiple particle species.

The method may further comprise a step of isolating each particle species based on the identity of the tag.

In accordance with the present invention, each nucleic acid probe species may comprise a distinct nucleic acid sequence.

Further in accordance with the present invention, each nucleic acid probe species may comprise a predetermined (given by the user or the manufacturer) nucleic acid sequence.

Methods of the present invention may be used with target concentration as low as $10^{-16}$ mole/L, $10^{-17}$ mole/L, $10^{-18}$ mole/L, or even $10^{-19}$ mole/L.

In one embodiment of the invention, the detection may be performed in aqueous conditions.

Also in accordance with the present invention, the contacting step may be performed in a volume of more than 1 µl or even in a volume in the milliliter range (e.g., of more than 1 milliliter).

In order to optimize the detection of the target, the particles may be concentrated to a smaller volume than the original sample volume before a signal is measured.

Also in order to optimize the detection of the target, the particles may be mixed with the sample and/or allowed sufficient period of time with the sample so as to enable capture of substantially all targets from the sample. Sampling may be performed over time and the contact between the particle and target may be stopped once the signal reaches a plateau.

In accordance with the present invention, the method may be used for diagnostic purposes or prognostic purposes. The method may also be used for quantification purposes (for quantifying the target(s)), for isolation purposes, (for isolating the target(s)) or for identification purposes (for identifying the target(s)).

The method may also be used for determining whether the target species is an optimal target or a suboptimal target. In such method, the signal emitted upon binding of the target species to the nucleic acid probe species may be compared to a reference signal obtained for an optimal target. As such, a signal equal or higher than the reference signal may be indicative of the presence of an optimal target in the sample, while a signal lower than the reference signal may be indicative of the presence of a sub-optimal target in the sample.

The target may be purified or substantially purified using the method described herein.

Hybridization may be performed under various stringency conditions in order to control the interaction between the probes and the targets. Higher stringency minimizes unspecific binding between capture probes and target molecules.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization also depends on the ability of denatured DNA target to reanneal with complementary strands when present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

Exemplary embodiment of "stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

An intrinsic advantage of using mobility controllable particles compared to conventional solid supports such as glass slides is the possibility of having the target-ready particles and the ssDNA target free in solution, therefore maximizing contact probability during detection (all sample volume is virtually accessible with the particles, less dependent on ssDNA diffusion when compared to classical hybridization at surfaces). This advantage is absent from previously reported solid support-based FCR techniques where FCR aggregates immobilized onto a static and planar surface (such as a glass slide) cannot be brought efficiently into contact with target molecules present in a large sample volume. Moreover, particles have more surface area per unit volume than planar surfaces (such as glass slides). The probe density (or aggregates density) may consequently be higher, and this larger reservoir of latent target-ready ssDNA-polymer units helps to maximize capture efficiency and detection sensitivity.

The target-ready particles of the present invention may be used in microfluidic systems (μTAS, micro-total analysis systems or lab-on-a-chip devices) allowing confinement of the particles (and by the same step, confinement of the target recognition element) in a small volume prior to the detection step. This advantage is absent from previously reported FCR-based techniques where freely diffusing FCR aggregates cannot be concentrated/confined in a finite volume after an efficient mixing with targets. The ability to decrease the final sample volume and discard the concomitants in the sample matrix generally translates into a better signal-to-noise ratio and better analytical performances. This aspect of the invention may be particularly important if the detection step is performed in a microscopic sample cell (i.e. microfluidic channels, etc.), as such structures can contribute significantly to the background signal due to increased scattering of the excitation light. Sample confinement also contributes to decrease the power requirements for the excitation source.

Different confinement methods/strategies may be used in conjunction with the present invention. The confinement of particles may be permanent (for example a covalent immobilization of particles on a solid support), temporary (for example using electromagnets to move/confine magnetic particles, or structures embedded within microfluidic channels to channel/direct/concentrate particles by hydrodynamic forces) or purely physical (for example using a weir in a microfluidic device against which to collect/stack the particles).

In the specific case (but not limited to) of microfluidic applications, the confinement of particles on structural features such as weirs may serve as a filtration system in order to preconcentrate particles and discard the sample matrix. This last point provides the pivotal advantage of limiting interactions between target-ready particles and non-specific material, thereby dynamically maximizing the discrimination between perfectly matched and non matched targets, by exploiting the lower binding equilibrium constant of non complementary material with the FCR aggregates.

The particles may therefore be used in diagnostic or prognostic methods for determining if a mammal is affected or is susceptible of being affected with a specific disease, disorder or condition. The method may comprise contacting a sample obtained from a mammal having or suspected of having a disease, disorder or condition with the particles described herein and determining the presence or absence of a desired target associated with such a disease, disorder or condition.

More particularly, the present invention provides a method for the diagnosis of a disease, disorder or condition in a mammal, the method may comprise;

a. providing a sample comprising a target or suspected of comprising a target associated with the disease, disorder or condition (obtained from the mammal);

b. contacting the sample (e.g., in a liquid form) with the target-ready particles of the present invention.

It is to be understood herein that the nucleic acid probe may comprise a nucleic acid (nucleotide/nucleoside) sequence capable of specific binding to the target associated with such disease, disorder or condition.

Alternatively, the nucleic acid probe may comprise a nucleic acid (nucleotide/nucleoside) sequence capable of specific binding to a target associated with a normal state.

An exemplary embodiment of a disease or condition which may be diagnosed using the particles described herein is one associated with aberrant protein expression (e.g., mutated protein, overexpression of protein).

Another exemplary embodiment of a condition or disease which may be readily diagnosed using the present invention may be one associated with a single nucleotide polymorphism (SNP). Therefore detection, quantification, identification, purification or isolation of SNPs or SNP gene products is encompassed herewith. Several exemplary embodiments of genetic variation associated with disease or conditions may be found in the Online Mendelian Inheritance in Man (OMIM) database. The OMIM database is a catalog of human genes and genetic disorders authored and edited by Dr. Victor A. McKusick and colleagues. Specific non-limiting examples of disease associated with genetic polymorphism may also be found, for example, in PCT applications published under Nos. WO07025085, WO06138696, WO06116867, WO06089185, WO06082570, WO0608267, WO04055196, WO04047767, WO04047623, WO04047514 and WO04042013.

Genetic polymorphism has been associated with variation in drug susceptibility within the population. For example, individuals carrying the wild type form or variants forms of CYP12C9 or VKORC1 respond differently to Acenocoumarol and Coumadin. Atomoxetine and irinotecan susceptibility also varies between individuals carrying the wild type of variant form of CYP2D6 and UGT1A1 respectively.

The present invention may thus be useful in the pharmacogenomic field where detection of a gene or a plurality of genes or gene products associated with a resistance or susceptibility to a drug will help in determining the proper therapy for the individual.

The present invention further provides for improved medico-legal (forensic) diagnostic assays. More specifically the affiliation of people and animals, "forensic" tools and other genetic testing tools.

The present invention also provides for improved clinical diagnostics of diseases or infections in a mammal.

The present invention also provides for improved biological warfare, bioweapons or bio-threat detection/identification. Specific non-limiting applications may include Anthrax alert in post-office, pandemic control at the point-of-entry of a country (airport security), and more largely for homeland security.

The present invention may thus be used for detecting or quantifying a pathogen or microorganism in a sample or for determining the identity of the pathogen or microorganism. The sample may not only be collected from an individual suspected of being contaminated with such pathogen or microorganism, but also it may be collected from any other source, including without limitation, the environment (e.g., air, soil, dust, water, etc.), an object, food, etc.

The present invention therefore provides for environmental and industrial screening, more specifically for the detection of genetically modified organisms, the detection of pathogenic agents, alimentary traceability, the identification of organisms of industrial interest (e.g., alimentary, pharmaceutical or chemical fermentation and soil decontamination) etc.

The present invention further relates to the use of a polymer or a complex made of a nucleic acid capture probe and the cationic polymer described herein in the making of target-ready mobile particles.

The present invention also relate to the use of the particle described herein for determining the presence or absence of a target in a sample, for isolating the target from the sample, for identifying the target or else.

The target-ready particles may thus be used not only for detecting the presence of a desired target, but also for quantifying a desired target or for the diagnosis or prognosis of a disease, disorder or condition in a mammal in need thereof etc.

The present invention therefore allows for the isolation of the target once detected using the method described herein.

The present invention also provides in a further aspect thereof, a method of making (manufacturing) the target-ready particle described herein.

The method of manufacturing may comprise for example, assembling the aggregates by mixing the nucleic acid capture probe comprising an immobilizing (attaching) means and a the cationic polymer under condition allowing for their electrostatic interaction, and immobilizing the aggregate onto the surface of a responsive (receptive) particle. The attachment of the aggregate to the particles may preferably be done under liquid conditions (e.g., aqueous conditions) which advantageously preserve the aggregate's structure.

It has been shown that the aggregates may retain photonic properties upon association with the particle during the manufacturing process.

The particles are considered "responsive" when allowing the binding of the capture probe though the attaching means. In an exemplary embodiment the particles may comprise for example a receptor or receptor-like molecule while the probe may comprise, as an attaching means, a ligand to that receptor (or vice-versa). Such types of interaction may be considered reversible. In another exemplary embodiment the particles may comprise a chemical group which may react with another chemical group found in the probe for a covalent-type attachment.

The innovative concept of grafting the aggregates onto particles dispersed in liquid media facilitates anchoring of the aggregates onto particles while stabilizing their structure. This also appears to preserve the intrinsic sensitivity of the aggregates, given that the volumetric detection limit obtained with particle-born FCR aggregates is closer to that obtained with FCR aggregates free in homogenous solution ($2\times10^{-19}$ vs. $3\times10^{-21}$ mole/L, respectively) than to that obtained with glass slide FCR ($5\times10^{-16}$ mole/L).

An additional advantage of the present invention is that each step, starting from aggregates grafting and including target capture and detection is performed in liquid media, maximizing the stability of the aggregate. As such, target capture and transduction may sustain multiple solution or buffer changes/washes. The assay also allows discarding the capture buffer and associated sample matrix, wash the particles and select an optimal detection buffer prior to the detection step. As the particles may be concentrated in a small volume, the sensitivity of detection may also be increased.

Figure 6:
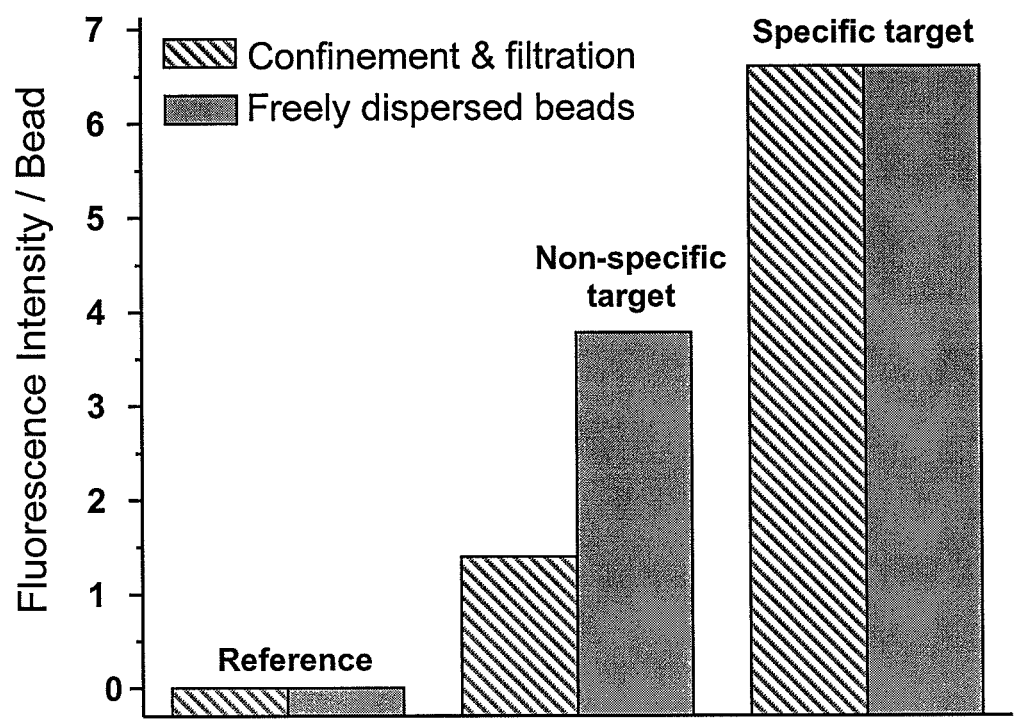
FIG. 6 is a graph illustrating the difference in detection specificity attained for beads measured while homogenously dispersed in a sample and for beads confined by a microfluidic wear and washed continuously by a flow of clean water. The fluorescence signal intensity was measured following the capture of 2000 purified and fractionated genomic DNA copies, with excitation at 408 nm and emission at 575 nm, for specific (i.e. perfectly matched ss-DNA probe and target) and non specific targets. The reference signal was measured from naked beads (aggregate-grafted particles without any target).

Another significant advantage of the present invention is that optical emission from the particles may be measured while the latter are simultaneously immobilized (e.g. against a microfluidic weir or in a microelectromagnetic trap) and submitted to a flow of clean media, e.g. pure water or buffer solution. Given the larger affinity of perfectly matched targets with the capture probes compared to that of mismatched targets, this dynamic flowing regime will act as to increase the ratio of perfectly matched to mismatched targets in the immobilized phase, and thus increase the detection selectivity beyond that attainable when the aggregates or particles are allowed to reach chemical equilibrium with the sample matrix (FIG. 6).

As used herein the terms "nucleic acid probe" or "nucleic acid capture probe" are used interchangeably.

As used herein the term "complementary" or "perfect complementary" with respect to nucleic acid molecules refers to a portion of the molecule that is able of base pairing with another nucleic acid molecule with a perfect (e.g., 100%) match. Base pairing is known in the art and may occur between modified or unmodified specific nucleotides through hydrogen bonds. As known in the art base pairing may occur between the base portion of a nucleotide, i.e., between adenine (A) and thymine (T), between adenine (A) and uracil (U), between guanine (G) and cytosine (C) or between inosine (I) and either one of uracil, adenine or cytosine.

As used herein the term "substantially complementary" with respect to nucleic acid molecules refers to a portion of the molecule that may be able of base-pairing with another nucleic acid molecule but which comprise at least one mismatch.

The terms "polynucleotide," "oligonucleotide," and "nucleic acid" are used interchangeably herein to refer to a polymeric form of nucleotides of any length, and may comprise ribonucleotides, deoxyribonucleotides, analogs thereof, or mixtures thereof. More particularly, the terms "polynucleotide," "oligonucleotide," and "nucleic acid" include polydeoxyribonucleotides and polyribonucleotides, including tRNA, rRNA, hRNA, and mRNA, whether spliced or unspliced.

As used herein the term "optimal target" refers to a target which is sought to be detected and/or which has the capacity to bind to the nucleic acid capture probe described herein. For example, the terms "optimal nucleic acid target" refers to a nucleic acid molecule which is sought to be detected.

The term "sub-optimal targets" or "unoptimal target" refers to a target which respectively has a reduced capacity to bind or is incapable of binding to the nucleic acid capture probe described herein as compared to an optimal target.

As used herein the term "unspecific molecule(s)" refers to a molecule which does not significantly bind to the nucleic acid molecule capture probe described herein or binds with the capture probe to an unsignificant extent.

Materials

All chemicals were purchased from Aldrich and were used without further purification. Labelled and unlabelled oligonucleotides were purchased from Integrated DNA Technologies, Inc. Cationic polythiophene was generously provided by Pr Mario Leclerc's research group (Chemistry Dept., Laval U.). On the basis of size-exclusion chromatography measurements calibrated with monodisperse polyvinylpyridinium samples, the polymer used in the experimental section is a polymer of formula Ia which has a number-average molecular weight of 11,000 with a polydispersity index of 2.0.

Magnetic microparticles were purchased from Dynal Biotech and were extracted from commercial storage solution in conformity with manufacturer recommendations. As an example of embodiment of the invention, a 20-mer capture probe was used for DNA detection (5'-biotin-CAT GAT TGA ACC ATC CAC CA-AlexaFluor546-3') in combination with two targets, one perfect complementary (3'-GTA CTA ACT TGG TAG GTGGT-5') which corresponds to a conserved region of the *Candida Albicans* yeast genome, and one sequence having two mismatches, (3'-GTA CTA ACT TCG AAG GTG GT-5'). The biotin-linker modification allowed high affinity binding of probes onto functionalized (streptavidin) particle surfaces.

As described in more details below, a single-stranded anionic nucleic acid capture probe functionalized with a suitable fluorescent acceptor molecule and a terminal group suitable for grafting onto particles was mixed with a cationic polymer and the resulting complex (dubbed duplex) was grafted to the surface of the particles as described below. Such labelled anionic capture probes and cationic polymer associate (preferably stoichiometrically) through electrostatic interactions and thus form nano-aggregates which may then be transferred onto the surface of controllable-mobility particles.

Target-Ready Particles Production

AF546-labeled probes were diluted into pure, autoclaved water to a final concentration of $2 \times 10^{-5}$ M of oligonucleotide strands (final volume of 10 µL) and mixed stoichiometrically (on a repeat unit basis) with the cationic water-soluble polythiophene (6.1 µL of $3.3 \times 10^{-5}$ M) in order to form the duplex. The mixture was then gently shaken during 10 minutes at 30° C. Target-ready particles were prepared by mixing the resulting duplex solution with magnetic particle (typically $10^6$ beads) in Tween20/LiCL/Tris buffer (30 µL) and stirring for 10 minutes at room temperature. Aggregate-grafted particles were then rinsed twice with Tween20 solution (0.5% v/v) and suspended in water until use. This protocol represents a reproducible method for aggregates formation and for the conservation of the detection properties (sensitivity and specificity) during transfer onto particles. Optimized aggregates functionalization protocol can be established with different particles surface such carboxylic, epoxide or aldehyde functionality and probe with terminal reactive group (amine, sulphide . . . ), using activator or not.

For the examples described herein, target hybridization was performed in pure water at 65° C.

Figure 2:
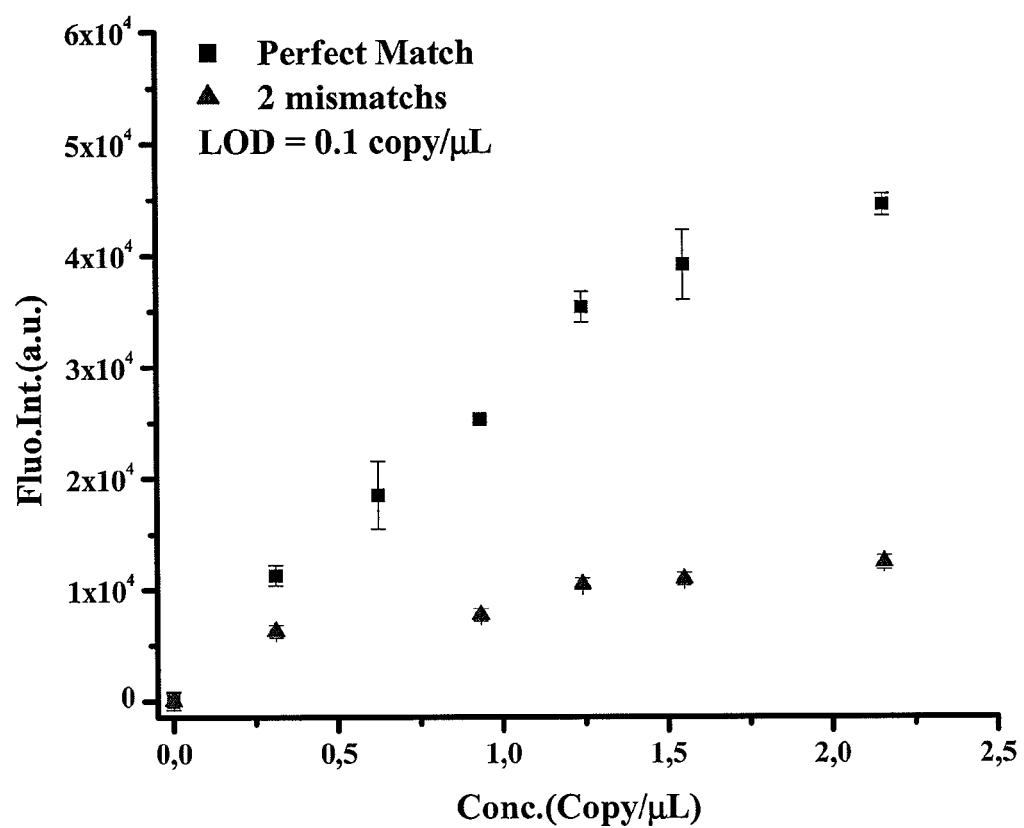
FIG. 2 is a graph illustrating the fluorescence intensity, measured at 575 nm with excitation at 425 nm, as a function of the target ss-DNA concentration (20-mer oligonucleotides); squares are the signal for perfect complementary targets and triangles are for 2-mismatch targets). Measurement was done with 200 beads (2.8 µm) suspended in solution in a 3-mL fluorometer cuvette. The limit of detection was calculated as 0.1 target copy per microliter, i.e. 15 target DNA molecules in a 150-µL probed volume ($2\times10^{-19}$ mole/L)

FIG. 2 shows typical results for the detection of targets in a highly diluted suspension, i.e. 200 particles suspended in a total volume of 3 mL (using a 3 mL fluorescence cuvette). The concentrations of the solutions used to generate these response curves varied from 0 to ~6500 copies of ssDNA targets diluted in the 3 mL volume (0 to $3.6 \times 10^{-18}$ mole/L). For each measurement, the total time required for hybridization and optical detection was less than five minutes. The detection limit (defined as 3 times the standard error on the signal measured from blank beads, i.e. aggregate-grafted particles without any target) calculated from these measurements was 15 target DNA molecules in the 150-µL effective probed volume ($2 \times 10^{-19}$ mole/L). Interestingly, this detection limit is closer to that measured previously for FCR aggregates free in homogenous solution using the same fluorometer, i.e. $3 \times 10^{-21}$ mole/L (JACS 2005) than to that reported for glass slide based FCR ($5\times10^{-16}$ mole/L), which tends to demonstrate that the one-pot procedure used to attach the aggregates to the particles (i.e. while the particles are dispersed in the same media used to form said aggregates) succeeds to preserve the intrinsic sensitivity of the aggregates.

Figure 3:
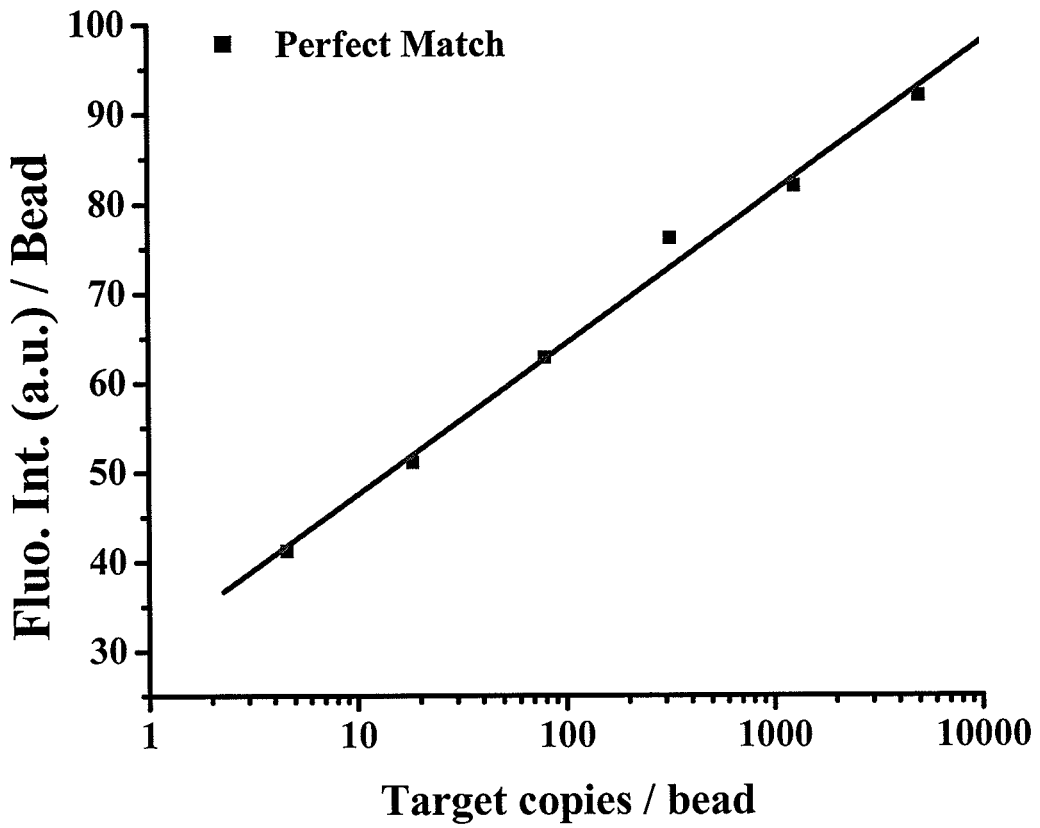
FIG. 3 is a graph illustrating the fluorescence intensity, measured at 575 nm with excitation at 408 nm, as a function of the number of perfect complementary ss-DNA targets (20-mer oligonucleotides) within the range from 0 to 5100 target molecules per bead (0 to $2.5\times10^{-19}$ mole). Measurements were done with an average of 30 beads confined in the center a micro-electromagnetic trap.

FIG. 3 shows the dynamic range for the optical detection of perfectly-matched 20-mer ssDNA target molecules captured on FCR-grafted magnetic particles initially dispersed in 55-80 µL samples (0 to 5100 target DNA per bead onto $7\times10^4$ beads) and then magnetically concentrated in a small and well-defined detection area, i.e. the center of a micro-electromagnetic trap (70 µm-diameter) (Anal. Chem. 78:4457-4464, 2006). Measurements were done with an average of 30 beads confined in the center of the trap. The semi-logarithmic curve is linear over at least 3 orders of magnitude in concentration.

Figure 4:
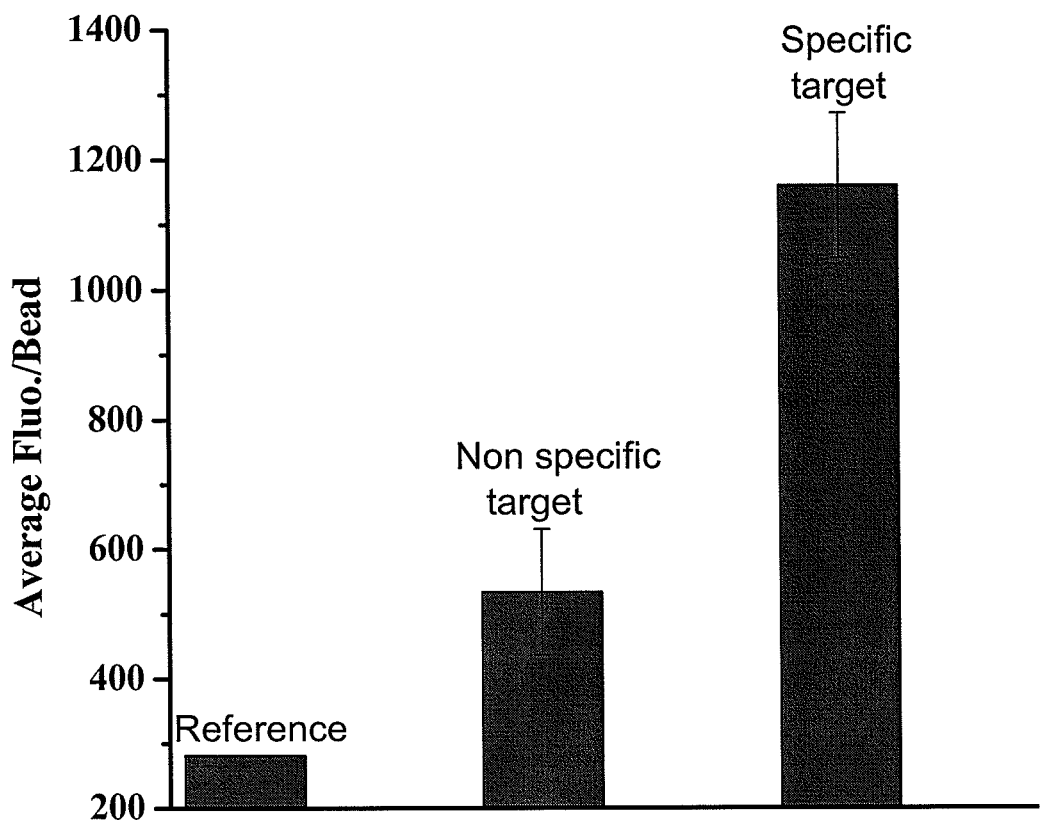
FIG. 4 is a graph illustrating the fluorescence intensity measured at 575 nm with excitation at 408 nm, for both specific (i.e. perfectly matched ss-DNA probe and target) and non specific genomic targets. The reference signal was measured from naked beads (aggregate-grafted particles without any target). Measurement was done with an average of 30 beads confined in the center of a micro-electromagnetic trap. The DNA in this example was obtained from the lysis of $10^3$ cells, fractionated in an ultrasonic bath (typical fragment length of 500-2000 DNA base pairs), summarily filtrated on a 0.2 µm membrane and used without further purification.

FIG. 4 shows typical results for the detection of target molecules captured on magnetic particles following the magnetic confinement of said particles in a well-defined detection area, i.e. the center of a micro-electromagnetic trap (70 µm-diameter) for both specific targets (i.e. perfectly matched ss-DNA probe and target) and non specific targets (i.e. genomic DNA extracted from similar cells but from which the targeted sequence was absent). The DNA in this example was obtained from the lysis of $10^3$ cells, fractionated in an ultrasonic bath (typical fragment length of 500-2000 DNA base pairs), summarily filtrated on a 0.2 µm membrane and used without further purification. This example demonstrates the detection specificity of particle-bound FCR aggregates for longer target DNA material typical of clinical or biological samples. Other experiments (results not shown) indicate that the detection specificity is preserved also for non sonicated DNA material.

Figure 5:
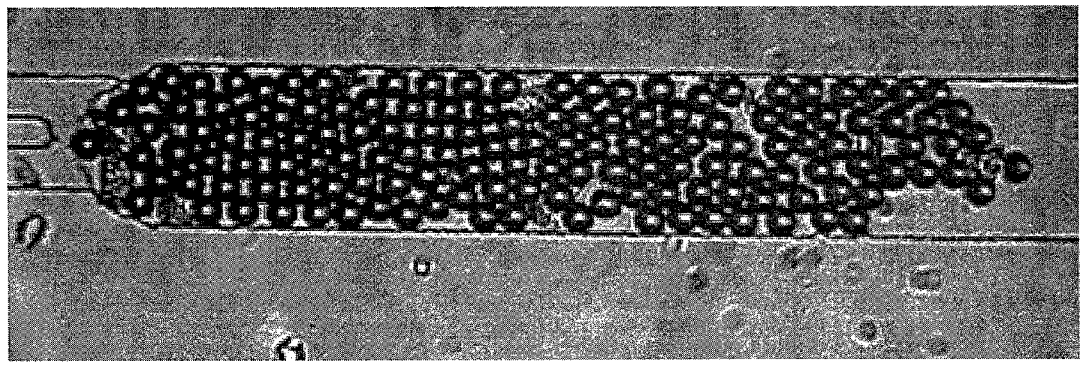
FIG. 5 is an optical image (10× magnification) showing beads collected and stacked against a weir within a microfluidic channel, illustrating a simple means of confinement of target-ready particles for optical detection.

FIG. 5 shows an optical image of a device that can be used to concentrate the mobility-controlled FCR-grafted particles prior to their optical detection by a physical/mechanical method other than magnetic, i.e. a weir located in a microfluidic channel.

FIG. 6 illustrates how a greater detection specificity can be obtained when the fluorescence signal is measured while the particles are spatially confined and submitted to continuous washing by pure water, as compared with measuring the signal from particles freely dispersed in the sample (200 beads dispersed in 3-mL cuvette, similar conditions that experiments reported in FIG. 2) and, hence, submitted to the presence of an excess of non-sequence specific DNA material from the sample matrix. In the former case, the particles were confined against a weir in a micro-fluidic device (as the one shown in FIG. 5) and the fluorescence signal was measured in the same manner as in the case of FIGS. 3 and 4 (i.e. signal collected from an area 70-µm in diameter at the bottom of a microfluidic channel). The DNA targets in this example were purified and fractionated genomic DNA targets (typical fragment length 500-2000 base pairs) initially dispersed in a 4 uL aqueous sample. The controllable mobility of FCR-grafted particles grants them the primordial advantage of changing their local chemical environment at will, to exploit, as shown in this example, the lower binding equilibrium constant of non complementary material with the FCR aggregates and hence dynamically maximizing the discrimination between perfectly matched and non matched targets.

Fluorescence Measurement

Although other apparatus and devices may be used, fluorescence measurements were performed with two custom fluorescence readers. Experiments with highly diluted particle concentrations were performed with a custom-made portable fluorometer tailored for the polythiophene sensor (described elsewhere, JACS 2004). Fluorescence detection of particles magnetically confined in µ-electro-magnetic traps and particles physically confined on a weir within a microfluidic device was performed with a custom-made fluorescence detection system dedicated to the collection of the optical signal coming from a solid support surface. For each apparatus, the excitation wavelength and the narrow bandpass of the interference emission filter (centered at 575 nm) overlapped well with the absorption of the polymer transducer and emission of AlexaFluor 546 spectral profiles, respectively.

Although the present invention has been described herein by way of exemplary embodiments, it can be modified without departing from the scope and the nature of the invention.

The present description refers to a number of documents, the content of which is herein incorporated by reference in their entirety.

REFERENCES

Dubus at al., PCR-free DNA detection using a magnetic bead-supported polymeric transducer and microelectromagnetic traps. Anal. Chem., 78, 4457-4464 (2006);

Ho et al., Direct molecular detection of nucleic acids by fluorescence signal amplification, J. Am. Chem. Soc., 127, 12673-12676 (2005);

Doré et al, Fluorescent polymeric transducer for the rapid, simple, and specific detection of nucleic acids at the zeptomole level. J. Am. Chem. Soc., 126, 4240-4244 (2004);

Ho et al., Colorimetric and fluorimetric detection of nucleic acids using cationic polythiophene derivatives, Angew. Chem. Int. Ed., 41, 1548-1551 (2002);

Najari at al., Reagentless ultrasensitive specific DNA array detection based on responsive polymeric biochips, Anal. Chem, 78, 7896-7899 (2006);

Doré et al., Characterization of superlighting Polymer-DNA aggregates: a fluorescence and light scattering study, Langmuir, 23, 258-264 (2007); Doré et al., Investigation of a Fluorescence Signal Amplification Mechanism Used for the Direct Molecular Detection of Nucleic Acids, J. Fluoresc., 16, 259-265 (2006).

Dalgleish et al., A possible structure of the casein micelle based on high resolution field-emission scanning electron microscopy, Int. Dairy J. 14, 1025-1031 (2004).

Ibrahim, S. F. and G. van den Engh, "Flow cytometry and cell sorting", Adv. Biochem. Engin. Biotechnol. (2007), 106, 19-39

U.S. Pat. No. 7,083,928 B2 to Leclerc at al.;

International patent application No. PCT/CA2007/000857 to Najari at al.;

U.S. Pat. No. 6,544,746 B2 to Heyduk;

U.S. Pat. No. 5,821,066 to Pyle et al.;

International patent application No. PCT/CA2006/000322 published under No. WO 2006/092063A1 to Leclerc et al., and;

European patent application No. EP05012568 published inder No. EP1 586904 A2 to Nakao et al.

Peytavi et al., Correlation between microarray DNA hybridization efficiency and the position of short capture probe on the target nucleic acid, BioTechniques 39, 89-96 (2005).

The invention claimed is:

1. A nano- or micro-sized particle comprising pre-assembled aggregates formed by the association of complexes comprising a nucleic acid probe and a polymer of formula A:

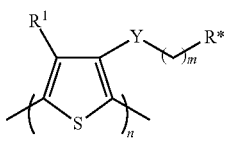

(formula A)

wherein:
m is an integer ranging for 2 to 3;
n is an integer ranging from 3 to 100;
R* is a quaternary ammonium;
Y is an oxygen atom or a methylene; and
R¹ is a methyl group or a hydrogen atom and wherein the aggregates are grafted to the surface of the nano- or micro-sized particle.

2. The nano- or micro-sized particle of claim 1, wherein the polymer comprises a formula selected from the group consisting of:

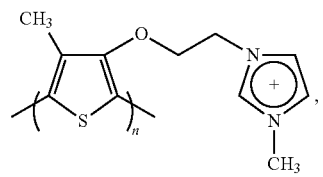

formula I

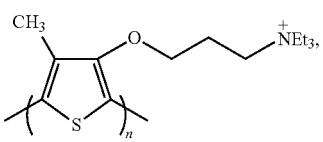

formula II

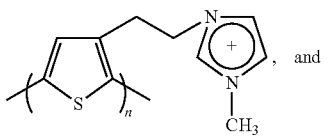

formula III, and

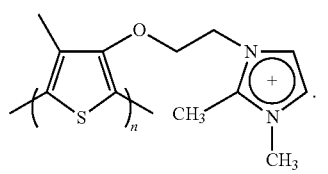

formula IV

3. The nano- or micro-sized particle of claim 2, wherein the polymer comprises a formula Ia

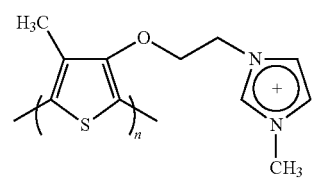

Ia wherein n is an integer ranging from 6 to 100.

4. The nano- or micro-sized particle of claim 1, wherein the nucleic acid probe is single-stranded.

5. The nano- or micro-sized particle of claim 1, wherein the nucleic acid probe comprises a label.

6. The nano- or micro-sized particle of claim 1, wherein the particle is capable of detecting a target at a concentration as low as $10^{-16}$ mole/L.

7. The nano- or micro-sized particle of claim 6, wherein the particle is capable of detecting a target at a concentration as low as $10^{-17}$ mole/L.

8. The nano- or micro-sized particle of claim 7, wherein the particle is capable of detecting a target at a concentration as low as $10^{-18}$ mole/L.

9. The nano- or micro-sized particle of claim 8, wherein the particle is capable of detecting a target at a concentration as low as $10^{-19}$ mole/L.

10. The nano- or micro-sized particle of claim 1, wherein the nucleic acid probe comprises a portion/section for specific recognition of a target.

11. The nano- or micro-sized particle of claim 10, wherein the particle is in an aqueous solution.

12. The nano- or micro-sized particle of claim 1, wherein the probe is RNA or DNA.

13. The nano- or micro-sized particle of claim 1, wherein the probe is from 8 to 50 bases long.

14. The nano- or micro-sized particle of claim 13, wherein the target has affinity for nucleic acids.

15. The nano- or micro-sized particle of claim 14, wherein the target comprises a nucleic acid.

16. The nano- or micro-sized particle of claim 15, wherein the nucleic acid is single-stranded or double stranded.

17. The nano- or micro-sized particle of claim 15, wherein the nucleic acid is DNA, RNA or DNA/RNA chimera.

18. The nano- or micro-sized particle of claim 17, wherein the DNA is a PCR amplicon, a genomic DNA or a restriction fragment.

19. The nano- or micro-sized particle of claim 14, wherein the target comprises a protein or a peptide.

20. The nano- or micro-sized particle of claim 19 wherein the target is unlabeled.

21. The nano- or micro-sized particle of claim 1, wherein every nucleic acid probes of the aggregates are identical.

22. The nano- or micro-sized particle of claim 1, wherein the aggregates provide for resonance energy transfer.

23. The nano- or micro-sized particle of claim 5, wherein the label comprises a fluorophore.

24. The nano- or micro-sized particle of claim 5, wherein the label comprises a chromophore.

25. The nano- or micro-sized particle of claim 1, wherein the nucleic acid probe and the polymer are in stoichiometric amount.

26. The nano- or micro-sized particle of claim 1, wherein the particle is a mobility-controllable particle.

27. The nano- or micro-sized particle of claim 1, wherein the particle comprises a tag allowing identification of the nucleic acid probe and/or target associated with the particle.

28. A composition comprising multiple nano- or micro-sized particle species, wherein each nano- or micro-sized particle species comprises pre-assembled aggregates formed by the association of complexes comprising a distinct nucleic acid probe species and a polymer of formula A:

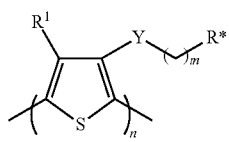

formula A wherein:
m is an integer ranging for 2 to 3;
n is an integer ranging from 3 to 100;
R* is a quaternary ammonium;
Y is an oxygen atom or a methylene; and
$R^1$ is a methyl group or a hydrogen atom
and wherein the aggregates are grafted to the surface of the nano- or micro-sized particles.

29. A method for detecting the presence or absence of a target in a sample comprising or suspected of comprising the target, the method comprising:
contacting the sample with a nano- or micro-sized particle comprising a pre-assembled aggregate formed by the association of complex comprising a nucleic acid probe and a polymer of formula A:

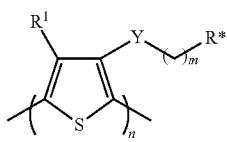

formula A wherein:
m is an integer ranging for 2 to 3;
n is an integer ranging from 3 to 100;
R* is a quaternary ammonium;
Y is an oxygen atom or a methylene; and
$R^1$ is a methyl group or a hydrogen atom,
allowing a sufficient period of time for the target to bind the nucleic acid probe and;
measuring or identifying a signal emitted upon binding of the target and the nucleic acid probe, and wherein the aggregate is grafted to the surface of the nano- or micro-sized particle.

30. The method of claim 29, wherein the target is at a concentration as low as $10^{-19}$ mole/L in the sample.

31. The method of claim 29, wherein the nucleic acid probe comprises a label.

32. The method of claim 29, wherein the detection is performed in aqueous conditions.

33. The method of claim 31, wherein the label is a fluorescent acceptor molecule.

34. The method of claim 29, wherein the aggregates provide for resonance energy transfer.

35. The method of claim 29, wherein the nano- or micro-sized particle is a mobility-controllable particle.

36. The method of claim 29, wherein the nano- or micro-sized particle comprises a tag allowing identification of the nucleic acid probe associated with the nano- or micro-sized particle.

37. The method of claim 29, wherein multiple nano- or micro-sized particles are concentrated to a smaller volume than the original volume of the contacting step and are submitted to a flow of clean media before measuring or identifying the signal.

38. The method of claim 29, wherein multiple nano- or micro-sized particles are mixed with the sample so as to enable capture of substantially all targets from the sample.

39. A method for the simultaneous detection of multiple target species from a sample, the method comprising:
contacting the sample with a composition comprising multiple nano- or micro-sized particle species, wherein each nano- or micro-sized particle species comprises pre-assembled aggregates formed by the association of complexes comprising a distinct nucleic acid probe species and a polymer of formula A:

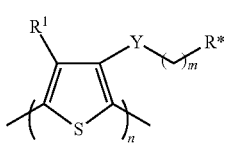

formula A wherein:
m is an integer ranging for 2 to 3;
n is an integer ranging from 3 to 100;
R* is a quaternary ammonium;
Y is an oxygen atom or a methylene; and
$R^1$ is a methyl group or a hydrogen atom,
allowing a sufficient period of time for the target species to bind the nucleic acid probe species and;
measuring or identifying a signal emitted upon binding of the target species and the nucleic acid probe species,
wherein each nano- or micro-sized particle species further comprises a distinct and selectable tag allowing its distinction among the multiple nano- or micro-sized particle species and wherein the aggregates are grafted to the surface of the nano- or micro-sized particle species.

40. The method of claim 39, further comprising a step of isolating each nano- or micro-sized particle species based on the identity of the tag.

41. The method of claim 39, wherein each nucleic acid probe species comprises a distinct nucleic acid sequence.

42. The method of claim 39, wherein each of the nucleic acid probe species comprises a label.

43. The method of claim 39, wherein the nano- or micro-sized particle is capable of detecting a target at a concentration as low as $10^{-19}$ mole/L.

44. The method of claim 43, wherein the label is a fluorescent acceptor molecule.

45. The method of claim 39, wherein the detection is performed in an aqueous solution.

46. The method of claim 39, wherein each aggregate of the nano- or micro-sized particle species is independently providing for resonance energy transfer.

47. The method of claim 39, wherein the nano- or micro-sized particle species are mobility-controllable.

48. The method of claim 39, wherein the nano- or micro-sized particle species are concentrated to a smaller volume than the original volume of the contacting step.

49. The method of claim 38, wherein the nano- or micro-sized particle species are confined in a delimited space and are submitted to a flow of clean media before the measuring or identifying step.

50. The method of claim 38, wherein the nano- or micro-sized particle species are mixed with the sample so as to enable capture of substantially all target species from the sample.

51. The method of claim 39, wherein the method is used for determining whether the target species is an optimal target or a suboptimal target, wherein the method further comprise comparing a signal emitted upon binding of the target species to the nucleic acid probe species to a reference signal obtained for an optimal target, whereby a signal equal or higher than the reference signal is indicative of the presence of an optimal target in the sample and whereby a signal lower than the reference signal is indicative of the presence of a sub-optimal target in the sample.

52. A method of manufacturing the nano- or micro-sized particle of claim 1, the method comprising assembling aggregates by mixing a nucleic acid capture probe comprising an attaching means and the polymer of formula A, formula I, formula Ia, formula II, formula III or formula IV under condition allowing for their electrostatic interaction, and associating the aggregates onto a surface of a receptive nano- or micro-sized particle and wherein each manufacturing step are performed in an aqueous solution.

53. The method of claim 52, wherein the aggregates are associated to the nano- or micro-sized particles in a native form obtained in solution and wherein the aggregates retain photonic properties upon association with the nano- or micro-sized particle.

54. The method of claim 52, wherein the nano- or micro-sized particles are dispersed in liquid media.

55. A kit comprising the nano- or micro-sized particle of claim 1.

* * * * *

UNITED STATES PATENT AND TRADEMARK OFFICE
CERTIFICATE OF CORRECTION

PATENT NO. : 8,765,369 B2  
APPLICATION NO. : 12/668388  
DATED : July 1, 2014  
INVENTOR(S) : Sebastien Dubus et al.

Page 1 of 1

It is certified that error appears in the above-identified patent and that said Letters Patent is hereby corrected as shown below:

In the Claims

In claim 49, column 24, line 50, delete "38" and insert -- 39 -- therefor.

In claim 50, column 24, line 54, delete "38" and insert -- 39 -- therefor.

Signed and Sealed this
Fourteenth Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,765,369 B2  
APPLICATION NO. : 12/668388  
DATED : July 1, 2014  
INVENTOR(S) : Sebastien Dubus Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 782 days.

Signed and Sealed this
Third Day of November, 2015

Michelle K. Lee
*Director of the United States Patent and Trademark Office*